US00PP35341P2

(12) United States Plant Patent
Van Dijk

(10) Patent No.: US PP35,341 P2
(45) Date of Patent: Aug. 22, 2023

(54) ***ANTHURIUM* PLANT NAMED 'AN2667176'**

(50) Latin Name: ***Anthurium andraeanum* L.**
Varietal Denomination: AN2667176

(71) Applicant: ANTHURA B.V., Bleiswijk (NL)

(72) Inventor: Jan Van Dijk, Bleiswijk (NL)

(73) Assignee: Anthura B.V., Bleiswijk (NL)

( * ) Notice: Subject to any disclaimer, the term of this patent is extended or adjusted under 35 U.S.C. 154(b) by 0 days.

(21) Appl. No.: 17/803,813

(22) Filed: Dec. 6, 2022

(51) Int. Cl.
*A01H 5/02* (2018.01)
*A01H 6/10* (2018.01)

(52) U.S. Cl.
USPC ..... Plt./365

(58) Field of Classification Search
USPC ..... Plt./365, 369
See application file for complete search history.

*Primary Examiner* — Susan McCormick Ewoldt
(74) *Attorney, Agent, or Firm* — Jondle & Associates, P.C.

(57) ABSTRACT

A new *Anthurium* plant named 'AN2667176' particularly distinguished by having medium blistered and weakly glossy, concave, red with white venation, orbicular-cordate, durable spathes that retain the original color for a very long period of time, dark green, ovate-cordate, durable leaves, light pink spadices with orange-green tips, rich in shoot formation, early and rich flowering continuously throughout the year, and a plant height of 28.0 cm to 32.0 cm is disclosed.

3 Drawing Sheets

Genus and species: *Anthurium andraeanum* L.
Variety denomination: 'AN2667176'.

BACKGROUND OF THE NEW PLANT

The present invention comprises a new and distinct variety of *Anthurium*, botanically known as *Anthurium andraeanum* L., and hereinafter referred to by the variety name 'AN2667176'. The new *Anthurium* plant is a product of a planned breeding program conducted by the inventor in Bleiswijk, the Netherlands. The objective of this breeding program was to create a new plant with a height of 28.0 cm to 32.0 cm having medium blistered and weakly glossy, concave, red with white venation, orbicular-cordate and durable spathes.

The new variety originated from a cross-pollination made in June 2014 in Bleiswijk, the Netherlands. The female parent was a red *Anthurium* pot plant designated '27775-03' (unpatented), and the male parent was an orange *Anthurium* pot plant designated '28516-01' (unpatented).

A single plant was selected from the progeny of the stated cross in May 2016. Asexual reproduction of the new variety by tissue culture in 2018 in Bleiswijk, the Netherlands, has demonstrated that the new variety reproduces true to type with all of the characteristics, as herein described, firmly fixed and retained through successive generations.

Community Plant Variety Rights for this variety have been applied for in the European Union on Nov. 19, 2021 (Application no. 2021/2985), by Applicant who obtained the subject matter disclosed directly from the inventor. 'AN2667176' has not been made publicly available or sold anywhere in the world prior to the effective filing date of this application with the exception of sales or disclosures made one year or less before the effective filing date of this claimed invention by Applicant who obtained 'AN2667176' directly from the inventor.

SUMMARY OF THE INVENTION

The following are the most outstanding and distinguishing characteristics of this new variety when grown under normal horticultural practices in Bleiswijk, the Netherlands:

1) Medium blistered and weakly glossy, concave, red with white venation, and orbicular-cordate spathes;
2) Light pink spadices with orange-green tips;
3) Green, ovate-cordate leaves;
4) Plant makes some extra shoots; and
5) Position of spathes compared to leaves is slightly above.

DESCRIPTION OF THE PHOTOGRAPHS

This new *Anthurium* plant is illustrated by the accompanying photographs which show the overall plant habit including blooms, buds, and foliage of the plant; the colors shown are as true as can be reasonably obtained by conventional photographic procedures. The photographs are of a 34-week-old plant grown in a greenhouse in Bleiswijk, the Netherlands, in August 2022. Colors in the photographs may differ from the color values cited in the detailed botanical description, which accurately describe the actual colors of the new variety.

DESCRIPTION OF THE NEW VARIETY

Figure 1:
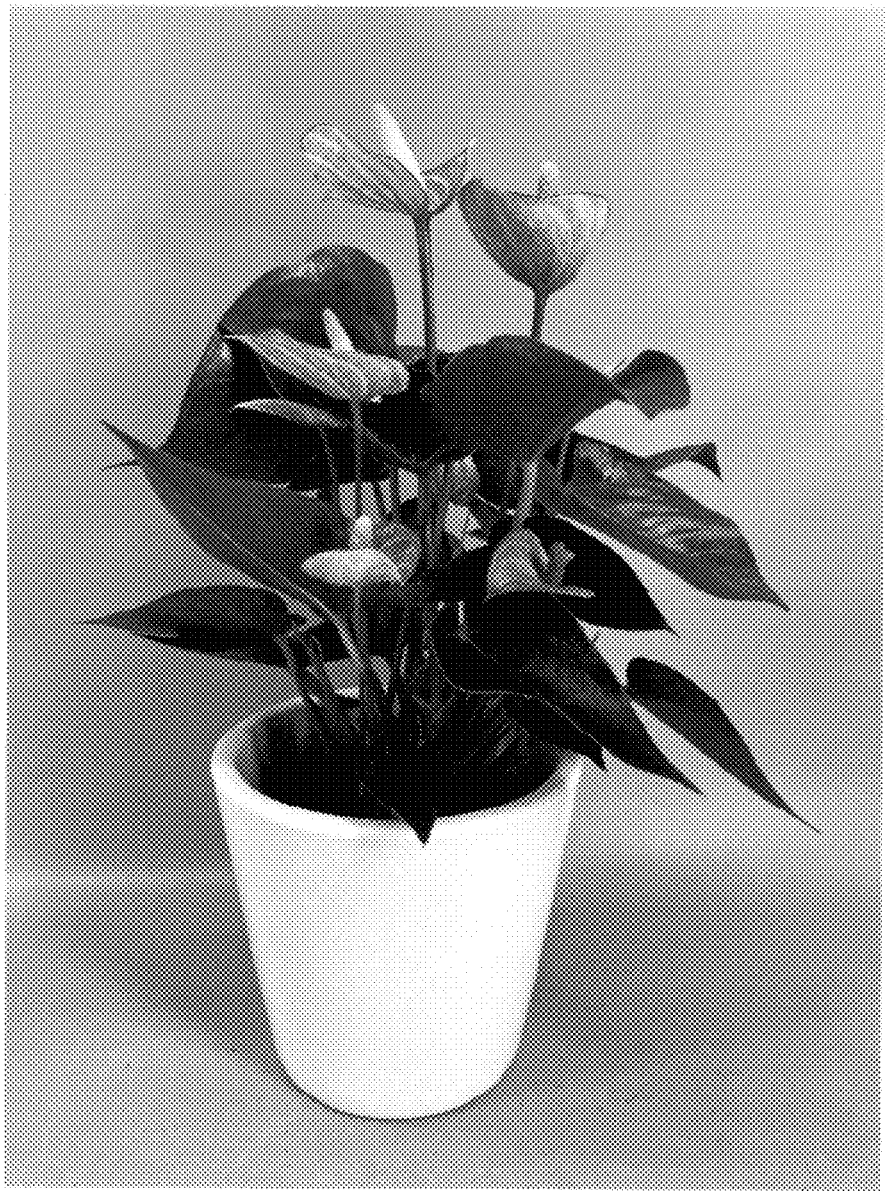
FIG. 1 shows the overall plant habit, including blooms, buds, and foliage.
Figure 2:
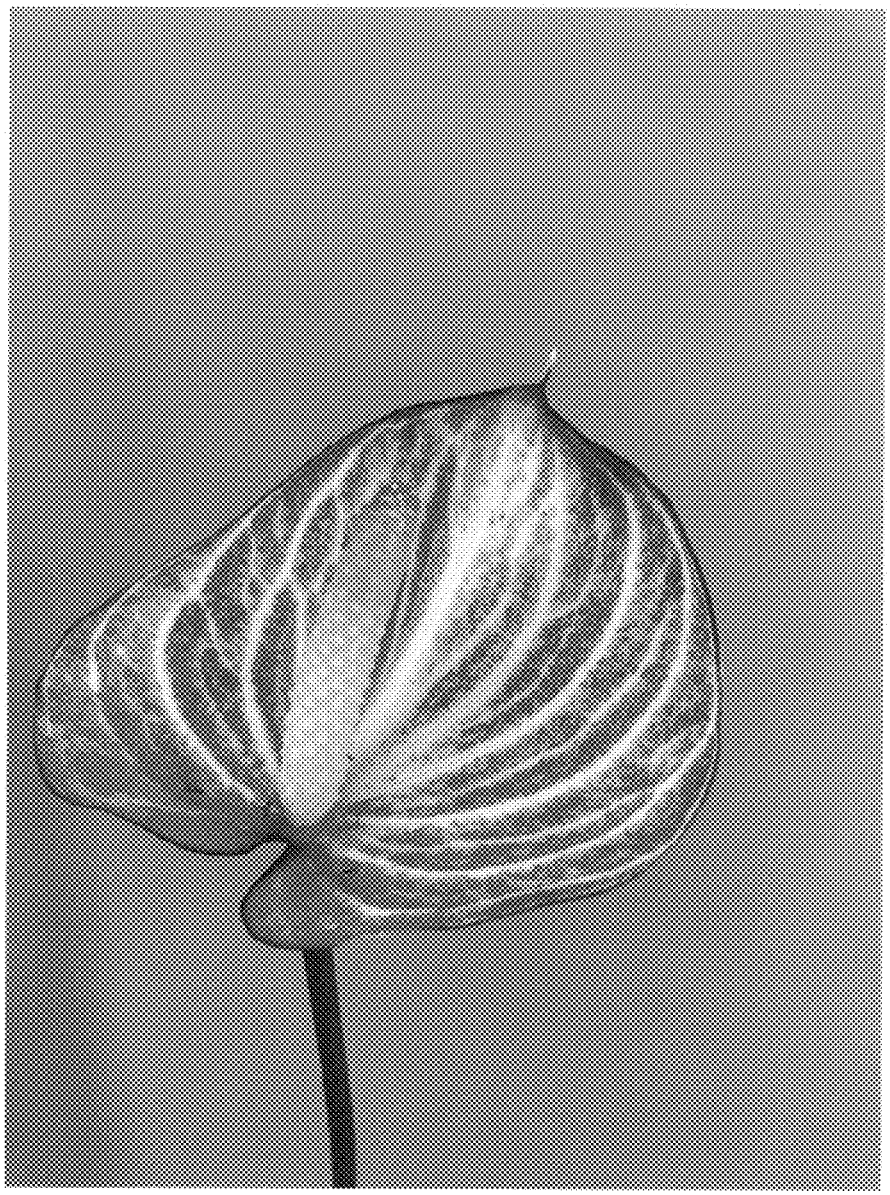
FIG. 2 shows a close-up of the mature spathe.
Figure 3:
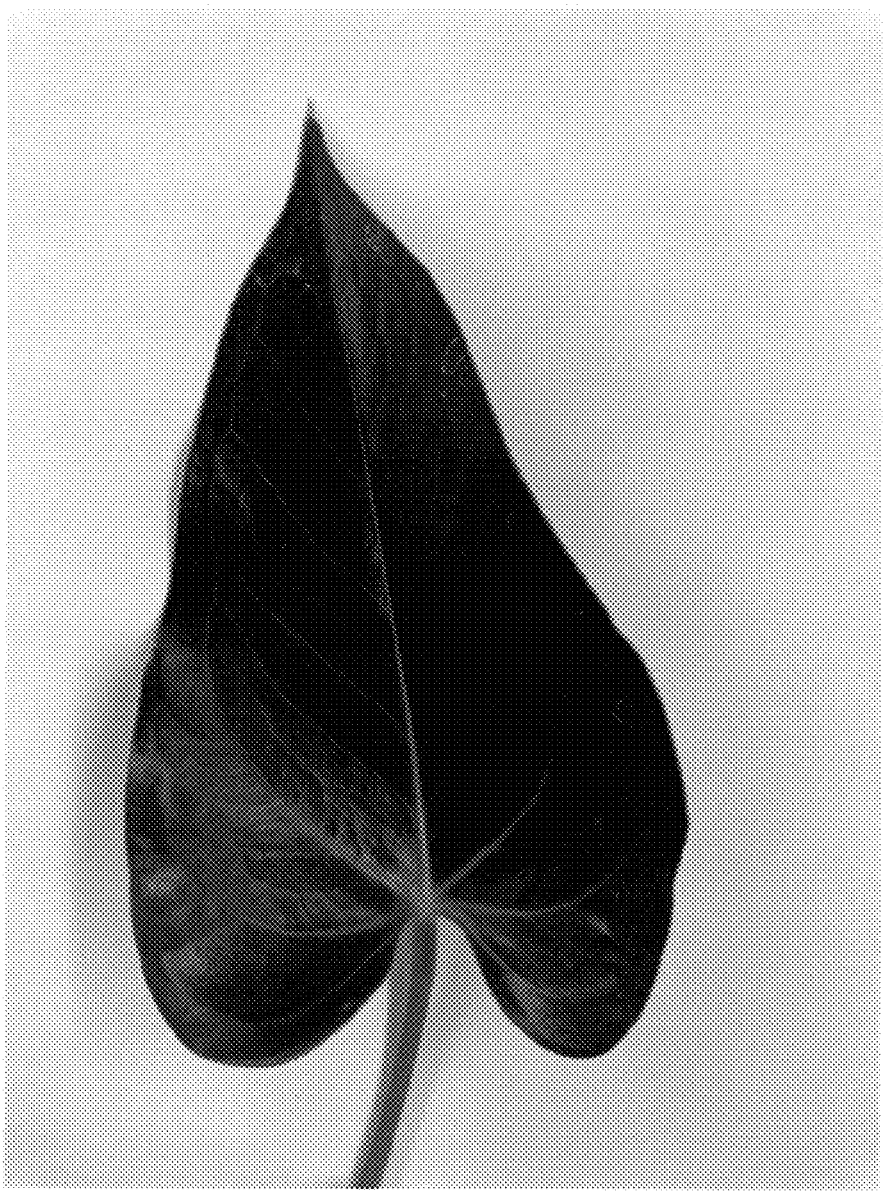
FIG. 3 shows a close-up of the upper leaf blade surface.

The following detailed description sets forth the distinctive characteristics of 'AN2667176'. The data which define these characteristics were collected from asexual reproductions carried out in Bleiswijk, the Netherlands. The plant history was taken on 34-week-old plants which were planted from tissue culture in 12-centimeter (diameter) pots and grown in a glass greenhouse between 19° C. and 24° C. Observations were made in August 2022. Color readings were taken under 5000 lux natural light in the greenhouse. Color references are primarily to The R.H.S. Colour Chart of The Royal Horticultural Society of London (R.H.S.) (2015).

DETAILED BOTANICAL DESCRIPTION

Classification:

*Family*.—Araceae.

*Botanical*.—*Anthurium andraeanum* L.

*Common name*.—*Anthurium*.

*Denomination*.—'AN2667176'.

Parentage:

*Female parent*.—*Anthurium* plant '27775-03' (unpatented).

*Male parent*.—*Anthurium* plant '28516-01' (unpatented).

Plant:

*Propagation*.—Tissue culture.

*Root description*.—Fleshy-creamy (RHS 161D) colored roots and small, hairy lateral roots having greenish-yellow (RHS 6A) colored root tips.

*Time to produce a finished flowering plant*.—32 to 36 weeks after planting in a 12-cm (diameter) pot.

*Growth habit*.—Upright.

*Height* (*measured from soil, including inflorescence*).—28.0 cm to 32.0 cm.

*Width* (*measured from leaf tips*).—29.0 cm to 31.0 cm.

Leaves:

*Immature leaves*.—Length: 11.0 cm to 14.0 cm. Width: 8.0 cm to 9.0 cm. Color: Upper surface: RHS 146A. Lower surface: RHS 146B. Texture (both upper and lower surfaces): Glossy, leathery, and thin.

*Mature leaves*.—Length (fully expanded): 15.0 cm to 17.0 cm. Width: 9.5 cm to 10.5 cm. Shape: Ovate cordate. Apex: Acuminate. Base: Cordate. Leaf blade angle with the petiole: Between 100 degrees and 120 degrees. Leaf margin: Entire. Color: Upper surface: RHS 147A. Lower surface: RHS 146B. Texture (upper surface): Leathery and thick. Texture (lower surfaces): Glossy, leathery, and thick. Venation: Pinnate veining; the mid-vein and primary veins (the veins that radiate out from the junction of petiole and leaf) protrude at the underside of the leaf blade. Venation color (both upper and lower surfaces): RHS 144A.

*Lobes*.—Present Arrangement: Leaf blade has two lobes extending past the petiole. The lobes are non-touching. Length of lobes of mature leaf blades: 3.0 cm to 3.5 cm. Width of lobes of mature leaf blades: 2.0 cm to 2.5 cm. Distance from petiole/leaf junction to highest point on lobes of mature leaf blades: 2.5 cm to 3.5 cm.

*Petiole*.—Cross-section: Round. Diameter: 0.3 cm to 0.4 cm. Length: 11.0 cm to 14.0 cm for a mature leaf size. Color: Mature leaf: RHS 144A. Immature leaf: RHS 144B. Cataphyll color surrounding the petiole: Outside: RHS 144A. Inside: RHS 145C.

*Geniculum*.—Length: 1.5 cm to 2.0 cm. Width: 0.4 cm to 0.5 cm. Color: RHS 144A.

Inflorescence:

*Arrangement*.—Single.

*Flowering habit* (*length of flowering season*).—Continuous.

*Number of inflorescences per plant*.—6 to 8.

*Fragrance*.—Absent.

*Longevity of inflorescence on plant*.—Over a year.

Spathe:

*Buds*.—The spathe is tightly rolled around the spadix and extrudes from the peduncle sheath. After the spathe is fully opened, the peduncle elongates some extra centimeters.

*Arrangement*.—Spathe angle with the peduncle is between 120 degrees and 130 degrees; the spathe stands on a wiry peduncle about 2.0 cm to 6.0 cm above the foliage.

*Shape*.—Orbicular cordate.

*Apex*.—Caudate.

*Base*.—Cordate.

*Texture*.—Medium blistered and weakly glossy.

*Margin*.—Undulated.

*Size*.—Length: 7.5 cm to 8.5 cm. Width: 8.0 cm to 9.0 cm.

*Lobes*.—Present. Arrangement: The spathe has two lobes extending past the peduncle. The lobes are non-touching. Length: 1.0 cm to 2.0 cm. Width: 2.5 cm to 3.5 cm.

*Color*.—Just fully open: Upper surface: RHS N45C with white (RHS 155C) venation. Lower surface: RHS N45D with white (RHS 157D) venation. This red color remains, for a very long period, at least more than 30 weeks after opening. The spathe turns green after some weeks.

Peduncle:

*Shape*.—Erect.

*Cross-section*.—Round.

*Length*.—20.0 cm to 23.0 cm.

*Diameter*.—0.3 cm to 0.4 cm.

*Color*.—RHS 144A.

Flowering time:

*General*.—One small, rooted, untreated tissue culture plant of 8.0 cm tall will flower, depending on the season, after 32 to 36 weeks and 6 to 7 blossoms appear. More blossoms appear after some additional weeks so that a full flowering and commercial plant will have 7 to 8 red spathes. Smaller blossoms may occur on immature plants.

Spadix:

*Size*.—Length: 4.0 cm to 5.0 cm (depending on flower size). Width (at apex): 0.6 cm to 0.7 cm. Width (at base): 0.7 cm to 0.8 cm.

*Shape*.—Columnar.

*Angle of spadix tip with peduncle*.—150 degrees to 170 degrees.

*Texture*.—When the spathe is unfurling, the spadix is smooth. When the spadix matures, small stigmata protrude. The stigmata are evenly distributed around the spadix. The spadix matures from base to top, slowly giving the spadix a somewhat rough appearance.

*Color*.—Immature: RHS 28C with green (RHS 151B) tip. Mature: RHS 36D. Ages to: RHS 144A.

Flowers:

*Quantity per spadix*.—130 to 160.

*Spadix flower arrangement*.—Bisexual, rounded in cross-section.

*Shape*.—Rounded.

*Size*.—Length: 0.05 cm to 0.10 cm. Diameter (maximum): 0.10 cm.

*Color*.—RHS 158C.

Reproductive organs:

*Stamens*.—Not visible.

*Pollen amount*.—Absent.

*Pistil*.—Quantity: 110 to 140. Length: Less than 0.01 cm. Color: RHS 158C.

*Style*.—Not observed to date.

*Stigma*.—Shape: Ovoid. Diameter: Less than 0.01 cm. Color: RHS 158C.

*Ovary*.—Rarely visible.

*Ovary color*.—Not measured.

Fruit and seed set: None observed to date.

Disease and pest resistance: No specific resistance or susceptibility observed to pathogens or pests common to *Anthurium* under commercial conditions to date.

COMPARISON WITH PARENTAL AND SIMILAR COMMERCIAL VARIETIES

'AN2667176' differs from the female parent plant '27775-03' (unpatented) in that 'AN2667176' has ovate-cordate leaves, orbicular-cordate spathes, and light pink basal part shortly before dehiscence of anthers, whereas '27775-03' has narrowly long-cordate leaves, cordate spathes, and white basal part shortly before dehiscence of anthers.

'AN2667176' differs from the male parent plant '28516-01' (unpatented) in that 'AN2667176' is concave in the cross section of middle zone of spathes, and the ground color of upper side of spathes is red, whereas '28516-01' is straight in the cross section of middle zone of spathes, and the ground color of upper side of spathes is orange.

'AN2667176' differs from the similar commercial variety 'ANTHFYTWAL' (U.S. Plant Pat. No. 29,774) in that 'AN2667176' has light pink basal part shortly before dehiscence of anthers and ovate-cordate leaves, whereas 'ANTHFYTWAL' has purplish-pink basal part shortly before dehiscence of anthers and deltoid leaves.

'AN2667176' differs from the similar commercial variety 'ANTHGNOBIC' (U.S. Plant Pat. No. 34,430) in that 'AN2667176' has ovate-cordate leaves, green cataphylls, and obtuse angle of distal part to the peduncle, whereas 'ANTHGNOBIC' has deltoid leaves, red cataphylls, and acute angle of distal part to the peduncle.

I claim:

1. A new and distinct variety of *Anthurium* plant named 'AN2667176', substantially as illustrated and described herein.

* * * * *